(12) United States Patent
Matsiev et al.

(10) Patent No.: US 6,957,565 B2
(45) Date of Patent: *Oct. 25, 2005

(54) METHOD AND APPARATUS FOR CHARACTERIZING MATERIALS BY USING A MECHANICAL RESONATOR

(75) Inventors: Leonid Matsiev, San Jose, CA (US); James Bennett, Santa Clara, CA (US); Eric McFarland, Santa Barbara, CA (US)

(73) Assignee: SYMYX Technologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/685,962

(22) Filed: Oct. 15, 2003

(65) Prior Publication Data

US 2004/0074302 A1 Apr. 22, 2004

Related U.S. Application Data

(63) Continuation of application No. 10/266,047, filed on Oct. 7, 2002, which is a continuation of application No. 10/201,181, filed on Jul. 23, 2002, which is a continuation of application No. 09/800,819, filed on Mar. 7, 2001, now Pat. No. 6,494,079, which is a division of application No. 09/133,171, filed on Aug. 12, 1998, now Pat. No. 6,393,895, which is a continuation-in-part of application No. 08/946,921, filed on Oct. 8, 1997, now Pat. No. 6,182,499.

(51) Int. Cl.$^7$ .............................................. G01N 29/02
(52) U.S. Cl. ............... 73/24.06; 73/31.06; 73/30.04; 73/32 A; 73/54.24; 73/54.38; 73/54.41; 73/61.49; 73/61.75; 73/61.79; 422/68.1
(58) Field of Search ............... 73/24.01, 24.03–24.06, 73/30.01, 30.04, 31.01, 31.02, 31.03, 31.05, 31.06, 32 A, 32 R, 53.01, 54.01, 54.02, 54.23, 54.41, 61.45, 61.75, 61.79, 579; 310/360, 316, 320; 422/68.1, 75, 98

(56) References Cited

U.S. PATENT DOCUMENTS

| | | | |
|---|---|---|---|
| 3,622,968 A | 11/1971 | Silverman | 367/9 |
| 3,718,032 A | 2/1973 | Gray | 73/626 |
| 3,778,757 A | 12/1973 | Houston | 367/11 |
| 3,902,365 A | * 9/1975 | Knauth | 73/861.03 |
| 3,903,732 A | 9/1975 | Rork et al. | |
| 4,342,936 A | 8/1982 | Marcus et al. | 310/330 |
| 4,349,881 A | 9/1982 | November et al. | 702/54 |
| 4,370,662 A | 1/1983 | Hou et al. | 347/75 |
| 4,391,338 A | 7/1983 | Patashnick et al. | 177/210 FP |

(Continued)

FOREIGN PATENT DOCUMENTS

| | | |
|---|---|---|
| EP | 0102490 | 3/1984 |
| EP | 0282251 | 9/1988 |
| EP | 0676638 | 10/1995 |

OTHER PUBLICATIONS

Fisch, M.R., et al., "Improved Acoustic Viscosimeter Technique", J. Acoust. Soc. Am., Sep. 1976, pp. 623–625, v. 60, No. 3.

Hiavay, J. and G.G. Guilbault, "Applications of the Piezoelectric Crystal Detector in Analytical Chemistry", Analytical Chemistry, Nov. 1977, pp. 1890–1898, v. 49, No. 13.

Kanazawa, K. Keiji and Joseph G. Gordon II, "The Oscillation Frequency of a Quartz Resonator in Contact with a Liquid", Analytica Chimica Acta, 1985, pp. 99–105, Elsevier Science Publishers B.V., Amsterdam.

(Continued)

Primary Examiner—Hezron Williams
Assistant Examiner—Rose M. Miller
(74) Attorney, Agent, or Firm—Dobrusin & Thennisch, PC

(57) ABSTRACT

A method for measuring properties of a fluid that includes oscillating a tuning fork resonator in a fluid. The invention is particularly suitable for in-line monitoring of various physical and electrical properties of fluids flowing in a conduit.

14 Claims, 8 Drawing Sheets

U.S. PATENT DOCUMENTS

| | | |
|---|---|---|
| 4,526,480 A | 7/1985 | Ward .......................... 374/117 |
| 4,543,829 A | 10/1985 | Lerch .......................... 73/626 |
| 4,596,697 A | 6/1986 | Ballato |
| 4,721,874 A | 1/1988 | Emmert ...................... 310/333 |
| 4,729,237 A | 3/1988 | Suzuki et al. |
| 4,734,609 A | 3/1988 | Jasime ....................... 310/315 |
| 4,741,200 A | 5/1988 | Hammerle ................. 73/54.25 |
| 4,760,351 A | 7/1988 | Newell et al. |
| 4,767,719 A | 8/1988 | Finian |
| 4,779,451 A | 10/1988 | Ezawa et al. .............. 73/53.01 |
| 4,783,987 A | 11/1988 | Hager et al. |
| 4,812,698 A | 3/1989 | Chida et al. ................ 310/330 |
| 4,890,480 A | 1/1990 | Young |
| 4,910,523 A | 3/1990 | Huguenin et al. .......... 342/179 |
| 4,922,745 A * | 5/1990 | Rudkin et al. .............. 73/32 A |
| 5,179,028 A | 1/1993 | Valie et al. .................. 436/524 |
| 5,191,791 A | 3/1993 | Gerardi et al. ............ 73/178 R |
| 5,201,215 A | 4/1993 | Granstaff et al. .......... 73/54.41 |
| 5,224,174 A | 6/1993 | Schneider et al. .......... 382/124 |
| 5,235,844 A | 8/1993 | Bonne et al. |
| 5,253,530 A | 10/1993 | Letcher, III .................. 73/602 |
| 5,283,037 A | 2/1994 | Baer et al. |
| 5,296,374 A | 3/1994 | Culshaw et al. |
| 5,306,644 A | 4/1994 | Myerholtz et al. |
| 5,338,416 A | 8/1994 | Mlcak et al. |
| 5,357,964 A | 10/1994 | Spivey et al. |
| 5,375,470 A | 12/1994 | Matsushima et al. |
| 5,421,190 A | 6/1995 | Brandle et al. |
| 5,454,045 A | 9/1995 | Perkins et al. |
| 5,455,475 A | 10/1995 | Josse et al. |
| 5,464,509 A | 11/1995 | Mlcak et al. |
| 5,469,369 A | 11/1995 | Rose-Pehrsson et al. |
| 5,488,866 A | 2/1996 | Ravel et al. |
| 5,524,636 A | 6/1996 | Sarvazyan et al. |
| 5,531,091 A | 7/1996 | Gademann et al. |
| 5,571,401 A | 11/1996 | Lewis et al. |
| 5,653,939 A | 8/1997 | Hollis et al. |
| 5,661,233 A | 8/1997 | Spates et al. |
| 5,698,089 A | 12/1997 | Lewis et al. |
| 5,705,399 A | 1/1998 | Larue |
| 5,734,098 A | 3/1998 | Kraus et al. |
| 5,741,961 A | 4/1998 | Martin et al. |
| 5,744,902 A | 4/1998 | Vig |
| 5,770,038 A | 6/1998 | Iwama et al. |
| 5,776,359 A | 7/1998 | Schultz et al. |
| 5,798,452 A | 8/1998 | Martin et al. |
| 5,827,952 A | 10/1998 | Mansure et al. |
| 5,852,229 A | 12/1998 | Josse et al. |
| 5,889,351 A | 3/1999 | Okumura et al. |
| 5,985,356 A | 11/1999 | Schultz et al. |
| 6,044,694 A | 4/2000 | Anderson et al. |
| 6,182,499 B1 | 2/2001 | McFarland et al. |
| 6,269,686 B1 | 8/2001 | Hahn et al. |
| 6,275,137 B1 | 8/2001 | Doppalapudi et al. |
| 6,306,658 B1 | 10/2001 | Turner et al. |
| 6,311,549 B1 | 11/2001 | Thundat et al. |
| 6,336,353 B2 | 1/2002 | Matsiev |
| 6,393,895 B1 | 5/2002 | Matsiev |
| 6,401,519 B1 | 6/2002 | McFarland et al. |
| 6,441,716 B1 | 8/2002 | Doppalapudi et al. |
| 6,494,079 B1 | 12/2002 | Matsiev et al. |
| 6,511,915 B2 | 1/2003 | Mlcak |
| 2002/0068488 A1 | 6/2002 | Tuller et al. |
| 2002/0070841 A1 | 6/2002 | Doppalapudi et al. |
| 2002/0137348 A1 | 9/2002 | MlCak |

OTHER PUBLICATIONS

Kipling, Arlin L and Michael Thompson, "Network Analysis Method Applied to Liquid–Phase Acoustic Wave Sensors", Anal. Chem., 1990, pp. 1514–1519, 62.

Michels, A. et al., "1 MHz Quartz Length Extension Resonator as a Probe for Scanning Near–Field Acoustic Microscopy", Thin Solid Films, 1995, pp. 172–175, 264.

Muramatsu, Hiroshi et al., "Computation of Equivalent Circuit Parameters of Quartz Crystals in Contact with Liquids and Study of Liquid Properties", Anal. Chem., 1988, pp. 2142–2146, 60.

Muramatsu, H. et al., "A Quartz Crystal Viscosity Sensor for Monitoring Coagulation Reaction and Its Application to a Multichannel Coagulation Detector", Biosensors & Bioelectronics, 1991, pp. 353–358, 6, Elsevier Science Publishers Ltd. England.

Nomura, T. and M. Iijima, "Electrolytic Determination of Nanomolar Concentrations of Silver in Solution with a Piezoelectric Quartz Crystal", Analytica Chimica Acta, 1981, pp. 97–102, 131, Elsevier Scientific Publising Company.

PCT International Search Report, dated Apr. 27, 1998.

Trolier et al., "Preparation of Chemically Etched Piezoelectric Resonators for Density Meters and Viscometers", Mat. Res. Bull., vol. 22, pp. 1267–1274 (1987).

News Release entitled Field Trials of the Viscosity & Fluid Density Tool (VFD) and webpage excerpt (2 pages).

Copending U.S. Appl. No. 10/201,181, filed Jul. 23, 2002, entitled Method and Apparatus for Characterizing Materials by Using a Mechanical Resonator (1012–122C2).

Nesbitt W. Hagood IV et al., "Development of Micro–Hydraulic Transducer Technology", 10th International Conference on Adaptive Structures and Technologies, Oct. 11–13, 1999, Paris, France.

Baltes, H. et al., "Sensors Update" (1996), pp. 38–83, vol. 2, Ch. 2.

Benes, E., et al., "Sensors based on piezoelectric resonators", Sensors and Actuators A 48 (1995), pp. 1–21.

Bret, A. M., et al., "Viscosity and Density Sensing with Ultrasonic Plate Waves", 8253a Sensors and Actuators—A Physical A 22 (1990) Mar., pp. 704–708, No. 1/3, Lausanne, CH.

Grate, J. W. et al., "Acoustic Wave Micro sensor", Analytical Chemistry, Nov. 1, 1993, pp. 940–948, vol. 65, No. 21.

Horine, B. N. and Malocha, D. C., "Equivalent Circuit Parameter Extraction of SAW Resonators", Utrasonics Symposium, (1990), pp. 477–482.

Martin, S. J. et al., "Characterization of a Quartz Crystal Microbalance with Simultaneous Mass and Liquid Loading", Analytical Chemistry, 1991, pp. 2272–2281, vol. 63, Nr. 20.

Thompson M. and Stone D.C., "Surface Launched Acoustic Wave Sensors", Chemical Analysis, 1997, pp. 1–196, vol. 144.

Sorab, J. and Salok, G.S., "Engine Oil Viscosity Sensors Using Disks Of PZT Ceramic as Electromechanical Vibrators", Society of Automotive Engineers, Inc., Copyright 1997, pp. 85–91.

* cited by examiner

CROSS-SECTION OF TSM RESONATOR PLATE

CROSS-SECTION OF TUNUNG FORK TINE

METHOD AND APPARATUS FOR CHARACTERIZING MATERIALS BY USING A MECHANICAL RESONATOR

CLAIM OF PRIORITY

This application is a continuation of 10/266,047, filed on Oct. 7, 2002, which is a continuation of 10/201,181, filed on Jul. 23, 2002, which is a continuation of 09/800,819, filed on Mar. 7, 2001, now U.S. Pat. No. 6,494,079, which is a divisional of 09/133,171, filed on Aug. 12, 1998, now U.S. Pat. No. 6,393,895, which is a CIP of 08/946,921, filed Oct. 8, 1997, now U.S. Pat. No. 6,182,499.

TECHNICAL FIELD

The present invention is directed to using mechanical oscillators for measuring various properties of fluids (including both liquids and vapors), and more particularly to a method and system using a mechanical oscillator (resonator) for measuring physical, electrical and/or chemical properties of a fluid based on the resonator's response in the fluid to a variable frequency input signal.

BACKGROUND ART

Companies are turning to combinatorial chemistry techniques for developing new compounds having novel physical and chemical properties. Combinatorial chemistry involves creating a large number of chemical compounds by reacting a known set of starting chemicals in all possible combinations and then analyzing the properties of each compound systematically to locate compounds having specific desired properties. See, for example, U.S. patent application Ser. No. 08/327,513 (published as WO 96/11878), filed Oct. 18, 1994, entitled "The Combinatorial Synthesis of Novel Materials", the disclosure of which is incorporated by reference.

The virtually endless number of possible compounds that can be created from the Periodic Table of Elements requires a systematic approach to the synthesizing and screening processes. Thus, any system that can analyze each compound's properties quickly and accurately is highly desirable. Further, such a system would be useful in any application requiring quick, accurate measurement of a liquid's properties, such as in-line measurement of additive concentrations in gasoline flowing through a conduit or detection of environmentally-offending molecules, such as hydrogen sulfide, flowing through a smokestack.

It is therefore an object of the invention to measure simultaneously both the physical and the electrical properties of a fluid composition using a mechanical resonator device.

It is also an object of the invention to detect differences clearly between two or more compounds in a fluid composition by using a mechanical resonator device to measure a composition's physical and electrical properties.

It is a further object of the invention to use a mechanical resonator device to monitor and measure a physical or chemical transformation of a fluid composition.

It is also an object of the invention to use a mechanical resonator device to detect the presence of a specific material in a fluid.

SUMMARY OF THE INVENTION

The present invention includes a method for measuring a property of a fluid composition using a tuning fork resonator, the method comprising:

placing the tuning fork resonator in the fluid composition such that at least a portion of the tuning fork resonator is submerged in the fluid composition;

applying a variable frequency input signal to a measurement circuit coupled with the tuning fork resonator to oscillate the tuning fork resonator;

varying the frequency of the variable frequency input signal over a predetermined frequency range to obtain a frequency-dependent resonator response of the tuning fork resonator; and determining the property of the fluid composition based on the resonator response.

The method can also measure a plurality of fluid compositions, wherein the fluid compositions are liquid compositions, using a plurality of tuning fork resonators, wherein the method further comprises:

providing an array of sample wells;

placing each of said plurality of liquid compositions in a separate sample well;

placing at least one of said plurality of tuning fork resonators in at least one sample well;

applying a variable frequency input signal to a measurement circuit coupled with each tuning fork resonator in said at least one sample wells to oscillate each tuning fork resonator associated with each of said at least one sample well;

varying the frequency of the variable frequency input signal over a predetermined frequency range to obtain a frequency-dependent resonator response of each tuning fork resonator associated with said at least one sample well; and analyzing the resonator response of each tuning fork resonator associated with said at least one sample well to measure a property of each liquid composition in said at least one sample well.

Accordingly, the present invention is directed primarily to a method using a mechanical piezoelectric quartz resonator ("mechanical resonator") for measuring physical and electrical properties, such as the viscosity density product, the dielectric constant, and the conductivity of sample liquid compositions in a combinatorial chemistry process. The detailed description below focuses primarily on thickness shear mode ("TSM") resonators and tuning fork resonators, but other types of resonators can be used, such as tridents, cantilevers, torsion bars, bimorphs, or membrane resonators. Both the TSM resonator and the tuning fork resonator can be used to measure a plurality of compounds in a liquid composition, but the tuning fork resonator has desirable properties that make it more versatile than the TSM resonator.

The mechanical resonator is connected to a measuring circuit that sends a variable frequency input signal, such as a sinusoidal wave, that sweeps over a predetermined frequency range, preferably in the 25–30 kHz range for the tuning fork resonator and in a higher range for the TSM resonator. The resonator response over the frequency range is then monitored to determine selected physical and electrical properties of the liquid being tested. Although both the TSM resonator and the tuning fork resonator can be used to test physical and electrical properties, the tuning fork resonator is an improvement over the TSM resonator because of the tuning fork's unique response characteristics and high sensitivity.

Both the TSM resonator and the tuning fork resonator can be used in combinatorial chemistry applications according to the present invention. The small size and quick response of the tuning fork resonator in particular makes it especially suitable for use in combinatorial chemistry applications, where the properties of a vast number of chemicals must be analyzed and screened in a short time period. In a preferred embodiment, a plurality of sample wells containing a plurality of liquid compositions are disposed on an array. A plurality of TSM or tuning fork resonators are dipped into the liquid compositions, preferably one resonator per composition, and then oscillated via the measuring circuit. Because the resonating characteristics of both the TSM resonator and the tuning fork resonator virtually eliminate the generation of acoustic waves, the size of the sample wells can be kept small without the concern of acoustic waves reflecting from the walls of the sample wells. In practice, the tuning forks can be oscillated at a lower frequency range than TSM resonators, making the tuning forks more applicable to real-world applications and more suitable for testing a wide variety of compositions, including high molecular weight liquids.

In another embodiment of the invention, the mechanical resonator is coated with a material to change the resonator's characteristics. The material can be a general coating to protect the resonator from corrosion or other problems affecting the resonator's performance, or it can be a specialized "functionalization" coating that changes the resonator's response if a selected substance is present in the composition being tested by the resonator.

To obtain a more complete range of characteristics for a selected fluid composition, multiple resonators having different resonator characteristics can be connected together as a single sensor for measuring the fluid composition. The resonator responses from all of the resonators in the sensor can then be correlated to obtain additional information about the composition being tested. By using resonators having different characteristics, the fluid composition can be tested over a wider frequency range than a single resonator. Alternatively, a single resonator that can be operated in multiple mechanical modes (e.g. shear mode, torsion mode, etc.) can be used instead of the multiple resonators. The resonator responses corresponding to each mode would be correlated to obtain the additional information about the composition.

The mechanical resonator system of the present invention, particularly a system using the tuning fork resonator, can also be used to monitor changes in a particular liquid by keeping the resonator in the liquid composition as it undergoes a physical and/or chemical change, such as a polymerization reaction. The invention is not limited to measuring liquids, however; the quick response of the tuning fork resonator makes it suitable for measuring the composition of fluid compositions, both liquid and vaporous, that are flowing through a conduit to monitor the composition of the fluid.

DETAILED DESCRIPTION OF THE PREFERRED EMBODIMENTS

The method and apparatus of the present invention focuses on using a mechanical resonator to generate and receive oscillations in a fluid composition for testing its characteristics in a combinatorial chemistry process or other process requiring analysis of the fluid composition's physical and/or chemical properties. Although the detailed description focuses on combinatorial chemistry and the measurement of a liquid composition's characteristics, the invention can be used in any application requiring measurement of characteristics of a fluid composition, whether the fluid is in liquid or vapor form. The fluid composition itself can be any type of fluid, such as a solution, a liquid containing suspended particulates, or, in some embodiments, even a vapor containing a particular chemical or a mixture of chemicals. It can also include a liquid composition undergoing a physical and/or chemical change (e.g. an increase in viscosity).

Figure 1A:
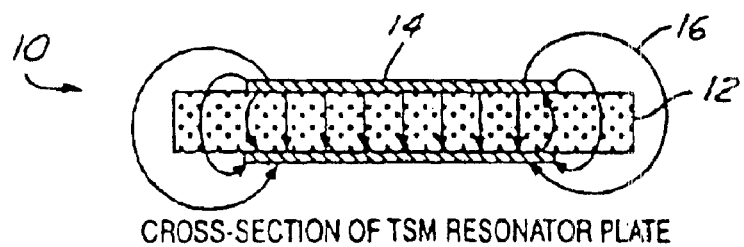
FIGS. 1a and 1b are cross-sectional views of a TSM resonator plate and a tuning fork resonator tine used in preferred embodiments of the present invention, respectively.
Figure 5A:
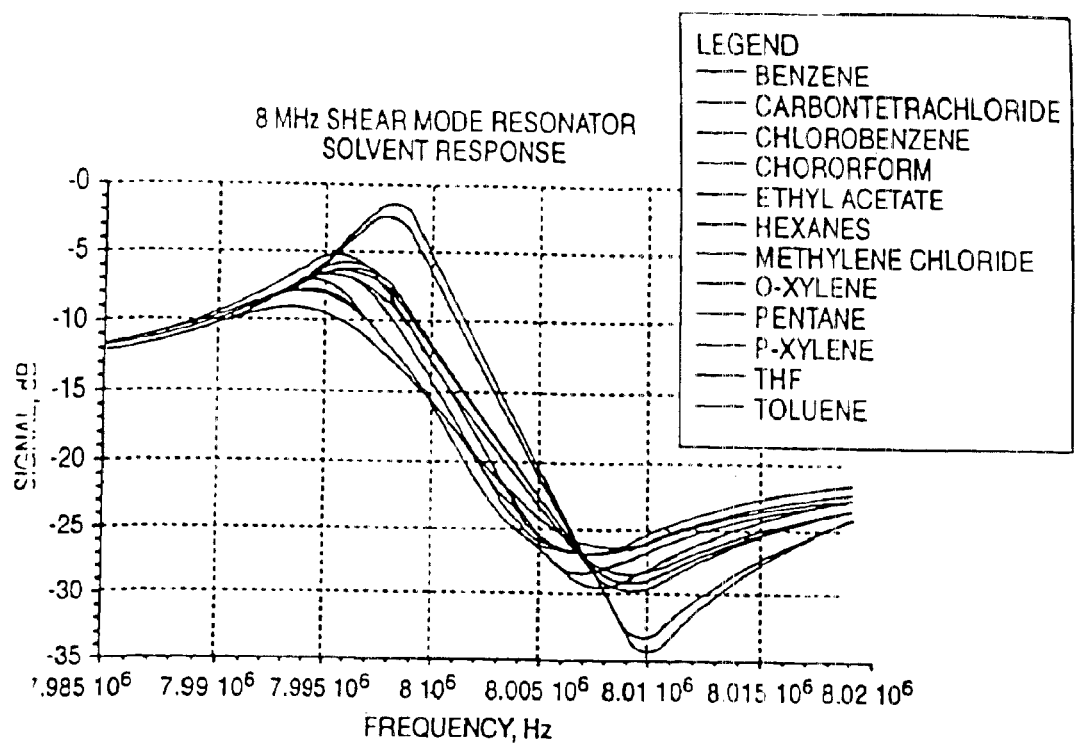
FIGS. 5a and 5b are examples of traces comparing the frequency responses of the TSM resonator and the tuning fork resonator of the present invention, respectively.

Mechanical resonators, such as thickness shear mode (TSM) quartz resonators 10, are used in the present invention for measuring various physical properties of fluid compositions, such as a liquid's viscosity, molecular weight, specific weight, etc., in a combinatorial chemistry setting or other liquid measurement application. Referring to FIG. 1a, TSM resonators 10 usually have a flat, plate-like structure where a quartz crystal 12 is sandwiched in between two electrodes 14. In combinatorial chemistry applications, the user first generates a "library", or large collection, of compounds in a liquid composition. Normally, each liquid composition is placed into its own sample well. A TSM resonator 10 connected to an input signal source (not shown) is placed into each liquid composition, and a variable frequency input signal is sent to each TSM resonator 10, causing the TSM resonator 10 to oscillate. The input signal frequency is swept over a predetermined range to generate a unique TSM resonator 10 response for each particular liquid. Because every compound has a different chemical structure and consequently different properties, the TSM resonator 10 response will be also be different for each compound. The TSM resonator response is then processed to generated a visual trace of the liquid composition being tested. An example of traces generated by the TSM resonator 10 for multiple liquid compositions is shown in FIG. 5a. Screening and analysis of each compound's properties can then be conducted by comparing the visual traces of each compound with a reference and/or with other compounds. In this type of application, the TSM resonator 10 serves both as the wave source and the receiver.

Two types of waves can be excited in liquids: compression waves (also called acoustic waves), which tend to radiate a large distance, on the order of hundreds of wavelengths, from the wave-generating source; and viscous shear waves, which decay almost completely only one wavelength away from the wave-generating source. In any liquid property testing, acoustic waves should be kept to a minimum because they will create false readings when received by the resonator due to their long decay characteristics. For typical prior art ultrasonic transducers/resonators, the resonator oscillation creates acoustic waves that radiate in all directions from the resonator, bounce off the sides of the sample well, and adversely affect the resonator response. As a result, the resonator response will not only reflect the properties of the liquid being measured, but also the effects of the acoustic waves reflecting from the walls of the sample well holding the liquid, thereby creating false readings. Using a sample well that is much greater than the acoustic wavelength does minimize the negative effects of acoustic waves somewhat, but supplying thousands of sample wells having such large dimensions tends to be impractical.

TSM resonators 10 primarily generate viscose shear waves and are therefore a good choice for liquid property measurement in combinatorial chemistry applications because they do not generate acoustic waves that could reflect off the sides of the sample wells and generate false readings. As a result, the sample wells used with the TSM resonators 10 can be kept relatively small, making it feasible to construct an array of sample wells for rapid, simultaneous testing of many liquids. The high stiffness of TSM resonators 10, however, require them to be operated at relatively high frequencies, on the order of 8–10 MHz. This stiffness does not adversely affect measurement accuracy for many applications, though, making the TSM resonator an appropriate choice for measuring numerous liquid compositions.

However, TSM resonators 10 can be somewhat insensitive to the physical properties of certain liquids because the load provided by the surrounding liquid is less than the elasticity of the resonator. More particularly, the high operating frequencies of TSM resonators 10 make them a less desirable choice for measuring properties of certain liquid compositions, particularly high-molecular weight materials such as polymers. When high frequency waves are propagated through high molecular-weight liquids, the liquids tend to behave like gels because the rates at which such large molecules move correspond to frequencies that are less than that of the TSM resonator's oscillations. This causes the TSM resonator 10 to generate readings that sometimes do not reflect the properties at which the liquids will actually be used (most materials are used in applications where the low-frequency dynamic response is most relevant). Although it would be more desirable to operate the TSM resonator 10 at lower frequencies so that laboratory conditions reflect real world conditions, the stiffness of the TSM resonator 10 and its resulting high operating frequencies can make operation at lower frequencies rather difficult. Further, even when the TSM resonator 10 can accurately measure a liquid's properties, the differences in the visual traces associated with different compositions are relatively slight, making it difficult to differentiate between compositions having similar structures, as shown in FIG. 5a.

TSM resonators and other plate-type resonators, while adequate, may not always be the best choice for measuring the electrical characteristics, such as the dielectric constant, of the liquid composition being measured. As shown in FIG. 1a, the cross-section of a TSM resonator 10 has the same structure as a flat capacitor, resulting in relatively little coupling between the electric field of the resonator and the surrounding composition. While there can be enough electrical coupling between the resonator and the composition to measure the composition's electrical properties, a greater amount of electrical coupling is more desirable for increased measurement accuracy. Electrical coupling will be explained in greater detail below when comparing the electrical characteristics between the TSM resonator 10 and the tuning fork resonator 20.

Figure 1B:
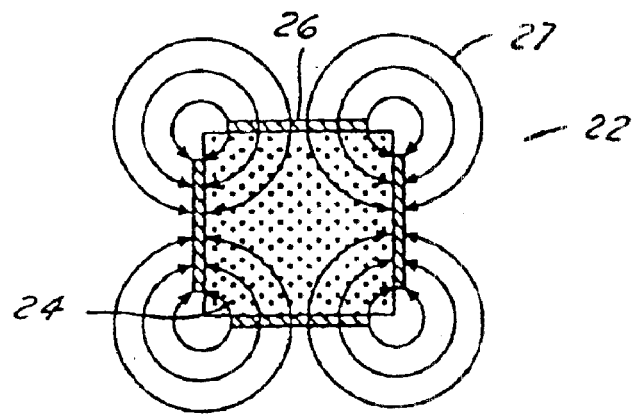
Figure 2:
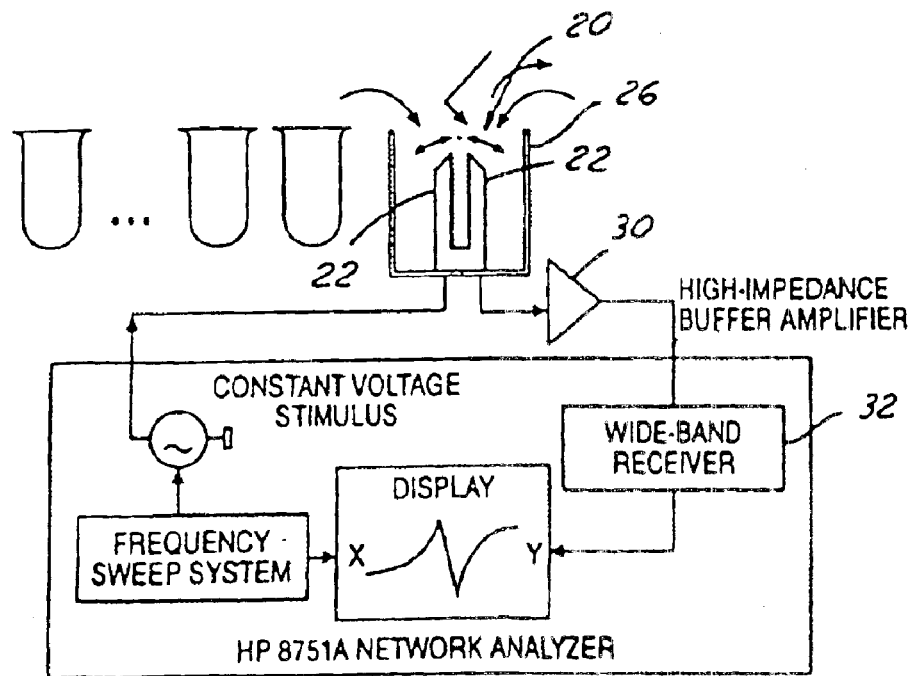
FIG. 2 is a block diagram illustrating an example of a composition testing system of the present invention.

FIGS. 1a and 1b show a cross-section of a TSM resonator plate 10 and a tuning fork tine 22, respectively. The tuning fork resonator 20 is preferably made from a quartz crystal 24 and has two tines 22, as represented in FIG. 2, each tine having the quartz crystal center 24 and at least one electrode 26 connected to the quartz crystal 24. The tuning fork tines 22 in the preferred structure have a square or rectangular cross-section such that the quartz crystal center 24 of each tine has four faces. The electrodes 26 are then attached to each face of the quartz crystal center 24, as shown in FIG. 1b. The method and system of the present invention can use any type of tuning fork resonator, such as a trident (three-prong) tuning fork or tuning forks of different sizes, without departing from the spirit and scope of the invention.

The cross-sectional views of the TSM resonator 10 and the tuning fork resonator 20 shown in FIGS. 1a and 1b also illustrate the relative differences between the electric coupling of each resonator with the surrounding liquid. Referring to FIG. 1a, the structure of the TSM resonator 10 is very flat, making it close to a perfect capacitor when it is placed in the liquid to be measured. As noted above, the quartz crystal 12 in the TSM resonator 10 is sandwiched between two electrodes 14, causing most of an electric field 16 to travel between the two electrodes through the quartz crystal 12. Because most of the electric field 16 is concentrated within the quartz crystal 12 rather than outside of it, there is very little electric coupling between the TSM resonator 10 and the surrounding liquid except at the edges of the resonator 10. While there may be sufficient electrical coupling to measure the electrical properties, such as the conductivity or dielectric constant, of the liquid composition being tested, a greater degree of coupling is desirable to ensure more accurate measurement.

By comparison, as shown in FIG. 1b, the structure of each tuning fork tine 22 allows much greater electrical coupling between the tine 22 and the surrounding liquid because the tuning fork tine's cross-sectional structure has a much different structure than a flat capacitor. Because the tuning fork tine 22 is submerged within the liquid being tested, an electric field 27 associated with each tine 22 does not concentrate in between the electrodes 24 or within the quartz crystal 24, but instead interacts outside the tine 22 with the surrounding liquid. This increased electrical coupling allows the tuning fork 20 to measure accurately the electrical properties of the liquid as well as its physical properties, and it can measure both types of properties simultaneously if so desired.

One unexpected result of the tuning fork resonator 20 is its ability to suppress the generation of acoustic waves in a liquid being tested, ensuring that the resonator's 20 physical response will be based only on the liquid's physical properties and not on acoustic wave interference or the shape of the sample well holding the liquid. As explained above, TSM resonators 10 minimize excitation of acoustic waves because it generates shear oscillations, which do not excite waves normal to the resonator's surface. As also explained above, however, the TSM resonator 10 requires high frequency operation and is not suitable for many measurement applications, particularly those involving high-molecular weight liquids.

Figure 3:
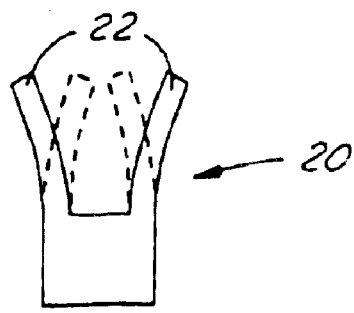
FIG. 3 is a representative diagram illustrating oscillation characteristics of the tuning fork resonator used in a preferred embodiment of the present invention.

Without wishing to be bound by any particular theory, the inventors believe that the tuning fork resonator 20 used in the present invention virtually eliminates the effects of acoustic waves without having to increase the size of the sample wells to avoid wave reflection. Tuning fork resonators 20, because of their shape and their orientation in the liquid being tested, contain velocity components normal to the vibrating surface. Thus, it was assumed in the art that tuning fork resonators were unsuitable for measuring liquid properties because they would generate acoustic waves causing false readings. In reality, however, tuning fork resonators 20 are very effective in suppressing the generation of acoustic waves for several reasons. First, the preferred size of the tuning fork resonator 20 used in the invention is much smaller than the wavelength of the acoustic waves that are normally generated in a liquid, as much as one-tenth to one-hundredth the size. Second, as shown in FIG. 3, the tines 22 of the tuning fork resonator 20 oscillate in opposite directions, each tine 22 acting as a separate potential acoustic wave generator. In other words, the tines 22 either move toward each other or away from each other. Because the tines 22 oscillate in opposite directions and opposite phases, however, the waves that end up being generated locally by each tine 22 tend to cancel each other out, resulting in virtually no acoustic wave generation from the tuning fork resonator 22 as a whole.

A simplified diagram of one example of the inventive mechanical resonator 20 system is shown in FIG. 2. Although the explanation of the system focuses on using the tuning fork resonator 20, the TSM resonator 10 described above can also be used for the same purpose. To measure the property of a given liquid, the tuning fork resonator 20 is simply submerged in the liquid to be tested. A variable frequency input signal is then sent to the tuning fork resonator using any known means to oscillate the tuning fork, and the input signal frequency is swept over a predetermined range. The tuning fork resonator's response is monitored and recorded. In the example shown in FIG. 2, the tuning fork resonator 20 is placed inside a well 26 containing a liquid to be tested. This liquid can be one of many liquids for comparison and screening or it can simply be one liquid whose properties are to be analyzed independently. Further, if there are multiple liquids to be tested, they can be placed in an array and measured simultaneously with a plurality of tuning fork resonators to test many liquids in a given amount of time. The liquid can also be a liquid that is undergoing a polymerization reaction or a liquid flowing through a conduit.

The tuning fork resonator 20 is preferably coupled with a network analyzer 28, such as a Hewlett-Packard 8751A network analyzer, which sends a variable frequency input signal to the tuning fork resonator 20 to generate the resonator oscillations and to receive the resonator response at different frequencies. The resonator output then passes through a high impedance buffer 30 before being measured by a wide band receiver 32. The invention is not limited to this specific type of network analyzer, however; any other analyzer that generates and monitors the resonator's response over a selected frequency range can be used without departing from the scope of the invention. For example, a sweep generator and AC voltmeter can be used in place of the network analyzer.

Figure 4A:
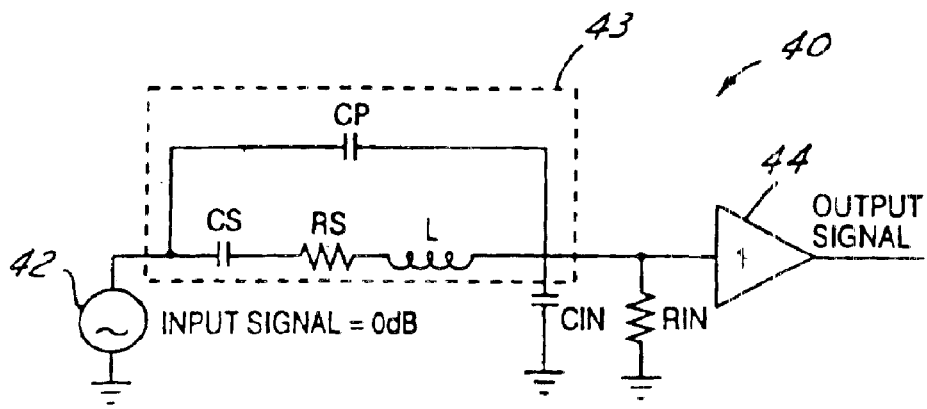
FIGS. 4a and 4b are simplified schematic diagrams illustrating a tuning fork resonator connection with the measurement circuit in a preferred embodiment of the present invention.
Figure 4B:
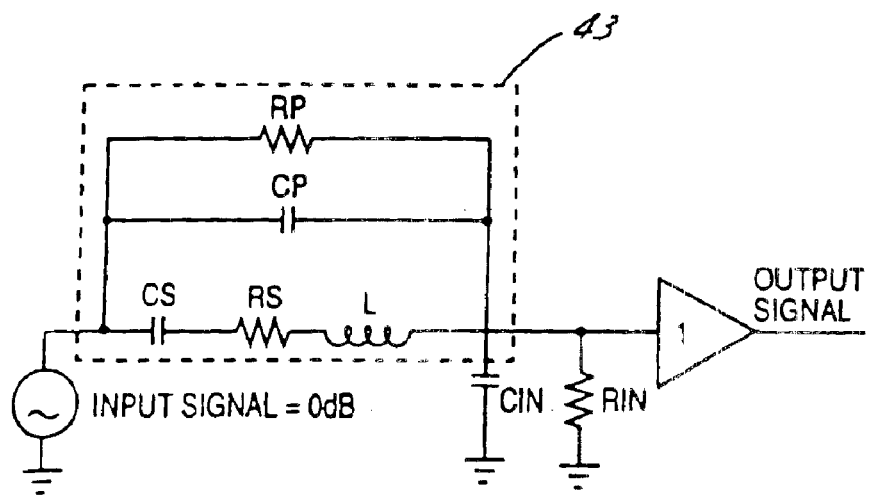

An equivalent circuit of the tuning fork resonator 20 and its associated measurement circuit is represented in FIGS. 4a and 4b. FIG. 4a represents an illustrative tuning fork resonator system that measures a liquid's viscosity and dielectric constant simultaneously, while FIG. 4b represents a tuning fork resonator system that can also measure a liquid's conductivity as well. Referring to FIG. 4a, the measurement circuit includes a variable frequency input signal source 42, and the resonator equivalent circuit 43 contains series capacitor Cs, resistor Rs, inductor L, and parallel capacitor Cp. The resonator equivalent circuit 43 explicitly illustrates the fact that the quartz crystal 24 in the tuning fork resonator 20 acts like a capacitor Cp. The representative circuit 40 also includes input capacitor Cin, input resistor Rin and an output buffer 44.

Figure 4C:
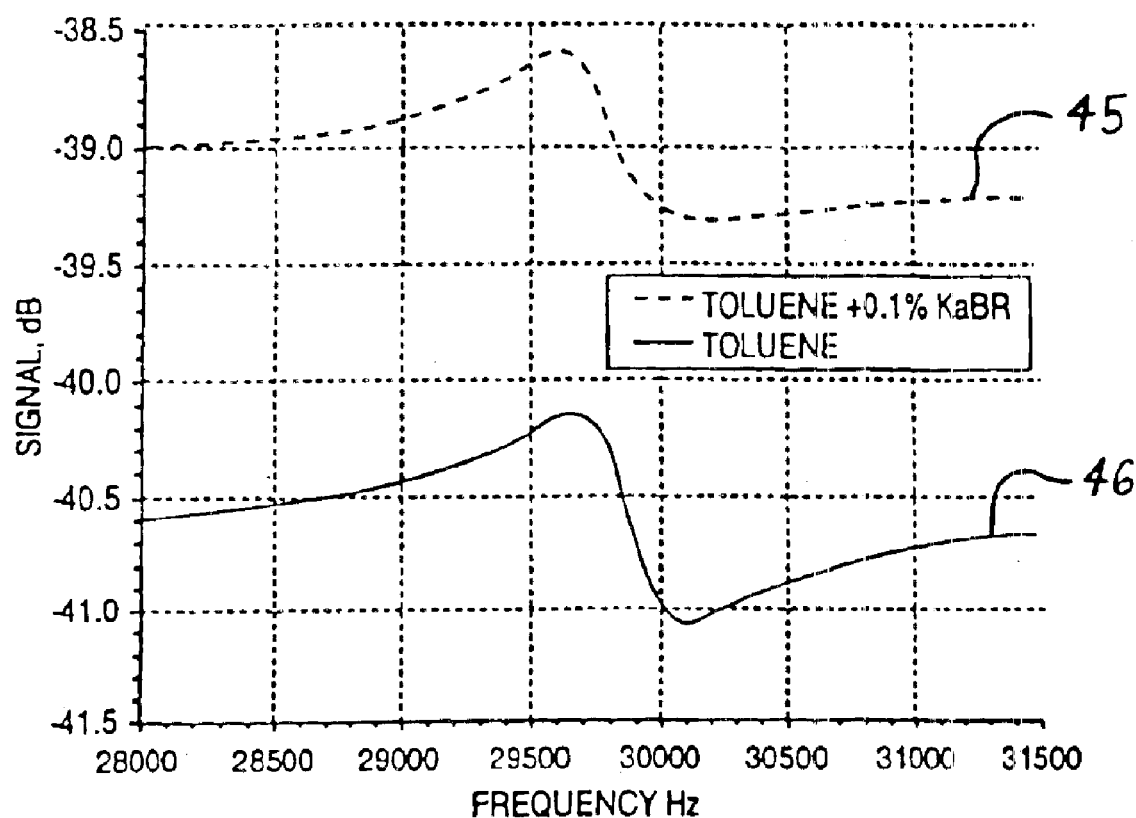
FIG. 4c illustrates a sample response of the representative circuit shown in FIG. 4b.

The representative circuit shown in FIG. 4b adds a parallel resistor Rp in parallel to capacitor Cp to illustrate a circuit that measures conductivity as well as dielectric constant and viscosity, preferably by comparing the equivalent resistance found in a given liquid with a known resistance found via calibration. These concepts will be explained in further detail below with respect to FIGS. 5a–b, 6a–b, 7a–b, and 8a–b. Rp represents the conductivity of the liquid being tested. The resistance can be calibrated using a set of liquids having known conductivity and then used to measure the conductivity of a given liquid. For example, FIG. 4c shows a sample trace comparing the resonator response in pure toluene and in KaBr toluene solution. A liquid having greater conductivity tends to shift the resonator response upward on the graph, similar to liquids having higher dielectric constants. However, unlike liquids with higher dielectric constants, a liquid having greater conductivity will also cause the resonator response to level out somewhat in the frequency sweep, as can be seen in the upper trace 45 between 30 and 31.5 kHz. In the example shown in FIG. 4c, the difference between the upper trace 45 and the lower trace 46 indicates that the equivalent resistance Rp caused by the additional KaBr in solution was about 8 mega-ohms.

EXPERIMENTAL EXAMPLES

FIGS. 5a–b, 6a–b, 7a–b and 8a–b are examples demonstrating the effectiveness of the invention. These figures show some differences between the frequency responses, for various liquid compositions, of the plate-type TSM resonator 10 and the tuning fork resonator 20. FIGS. 5a, 6a, 7a and 8a are examples using the TSM resonator 10, and FIGS. 5b, 6b, 7b and 8b are examples using the tuning fork resonator 20.

The experimental conditions for generating the example tuning fork resonator traces in FIGS. 5b, 6b, 7b, and 8b are described below. The experimental conditions for generating the comparative TSM resonator traces in FIGS. 5a, 6a, 7a and 8a are generally similar to, if not the same as, the conditions for the tuning fork resonator except for, if needed, minor modifications to accommodate the TSM resonator's particular geometry. Therefore, for simplicity and clarity, the TSM resonator's particular experimental conditions will not be described separately.

All of the solvents, polymers and other chemicals used in the illustrated examples were purchased from Aldrich, and the polymer solutions were made according to standard laboratory techniques. Dry polymers and their corresponding solvents were weighed using standard balances, and the polymer and solvent were mixed until the polymer dissolved completely, creating a solution having a known concentration. The solutions were delivered to and removed from a 30 ul stainless steel cylindrical measurement well that is long enough to allow a tuning fork resonator to be covered by liquid. Liquid delivery and removal to and from the well was conducted via a pipette or syringe.

Before any experiments were conducted with the solutions, the tuning fork resonator response in air was measured as a reference. The actual testing processes were conducted in a temperature-controlled laboratory set at around 20 degrees Centigrade. Once the liquid was delivered to the well, the tuning fork was placed in the well and the system was left alone to allow the temperature to stabilize. Alternatively, the tuning fork can be built into a wall portion or a bottom portion of the well with equally accurate results. The tuning fork was then oscillated using the network analyzer. The resonator response was recorded during each measurement and stored in a computer memory. The measured response curve was fitted to a model curve using an equivalent circuit, which provided specific values for the equivalent circuit components described above with respect to FIGS. 4a and 4b and the traces in FIGS. 6a through 8b.

After the measurement of a given solution was completed, the resonator was kept in the well and pure solvent was poured inside the well to dissolve any polymer residue or coating in the well and on the tuning fork. The well and tuning fork were blown dry using dry air, and the tuning fork response in air was measured again and compared with the initial tuning fork measurement to ensure that the tuning fork was completely clean; a clean tuning fork would give the same response as the initial tuning fork response. Note that the above-described experimental conditions are described only for purposes of illustration and not limitation, and those of ordinary skill in the art would understand that other experimental conditions can be used without departing from the scope of the invention.

Although both the TSM resonator 10 and the tuning fork resonator 20 are considered to be part of the method and system of the present invention, the tuning fork resonator 20 has wider application than the TSM resonator 10 and is considered by the inventors to be the preferred embodiment for most measurement applications because of its sensitivity, availability and relatively low cost. For example, note that in FIGS. 5a and 5b, the frequency sweep for the TSM resonator 10 is in the 8 MHz range, while the frequency sweep for the tuning fork resonator 20 of the present invention is in the 25–30 kHz range, several orders of magnitude less than the TSM resonator frequency sweep range. This increases the versatility and applicability of the tuning fork resonator 20 for measuring high molecular weight liquids because the operating frequency of the tuning fork resonator 20 is not high enough to make high molecular weight liquids act like gels. Further, because most applications for the solutions are lower frequency applications, the laboratory conditions in which the liquid compositions are tested using the tuning fork resonator 20 more closely correspond with real-world conditions.

Also, the operating frequency of the tuning fork resonator 20 varies according to the resonator's geometry; more particularly, the resonance frequency of the tuning fork 20 depends on the ratio between the tine cross-sectional area and the tine's length. Theoretically, it is possible to construct a tuning fork resonator 20 of any length for a given frequency by changing the tuning fork's cross-sectional area to keep the ratio between the length and the cross-section constant. In practice, however, tuning fork resonators 20 are manufactured from quartz wafers having a few selected standard thicknesses. Therefore, the cross-sectional area of the tuning fork 20 tends to be limited based on the standard quartz wafer thicknesses, forcing the manufacturer to change the tuning fork's resonating frequency by changing the tine length. These manufacturing limitations must be taken into account when selecting a tuning fork resonator 20 that is small enough to fit in minimal-volume sample wells (because the chemicals used are quite expensive) and yet operates at a frequency low enough to prevent the tested liquids from acting like gels. Of course, in other applications, such as measurement of liquids in a conduit or in other containers, the overall size of the tuning fork resonator 20 is not as crucial, allowing greater flexibility in selecting the size and dimensions of the tuning fork resonator 20. Selecting the actual tuning fork dimensions and designing a tuning fork resonator in view of manufacturing limitations are tasks that can be conducted by those of skill in the art after reviewing this specification.

Figure 5B:
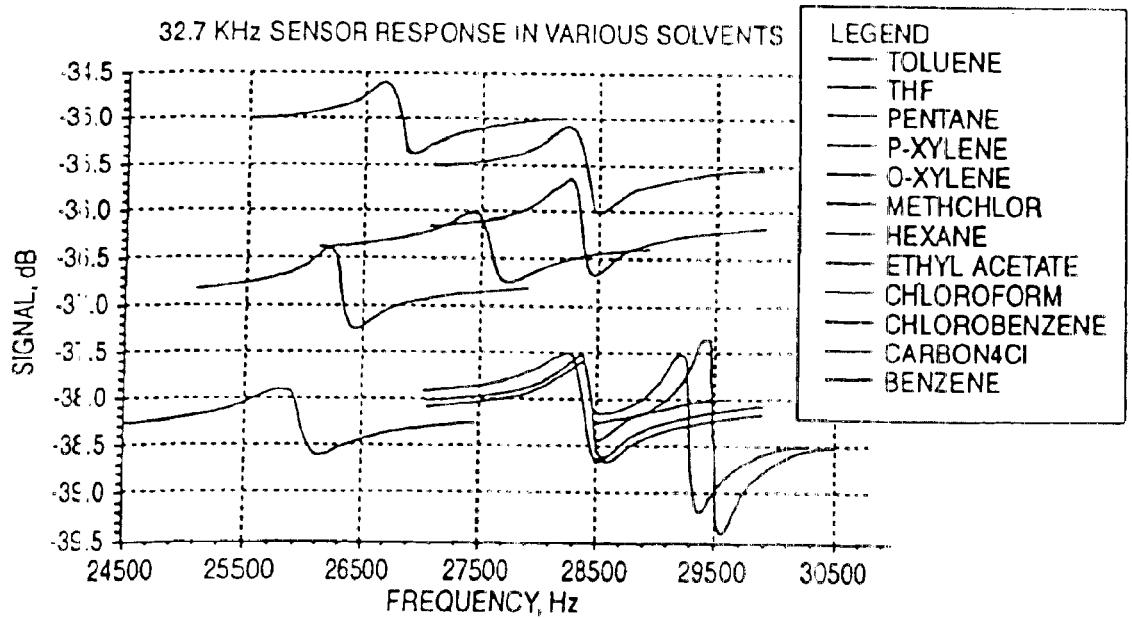

Referring to FIGS. 5a and 5b, the solutions used as examples in FIGS. 5a and 5b have somewhat similar structures and weights. As a result, the TSM resonator responses for each solution, shown in FIG. 5a, create very similar traces in the same general range. Because the traces associated with the TSM resonator 10 overlap each other to such a great extent, it is difficult to isolate and compare the differences between the responses associated with each solution. By comparison, as shown in FIG. 5b, the increased sensitivity of the tuning fork resonator 20 causes small differences in the chemical structure to translate into significant differences in the resonator response. Because the traces generated by the tuning fork resonator 20 are so distinct and spaced apart, they are much easier to analyze and compare.

Figure 6A:
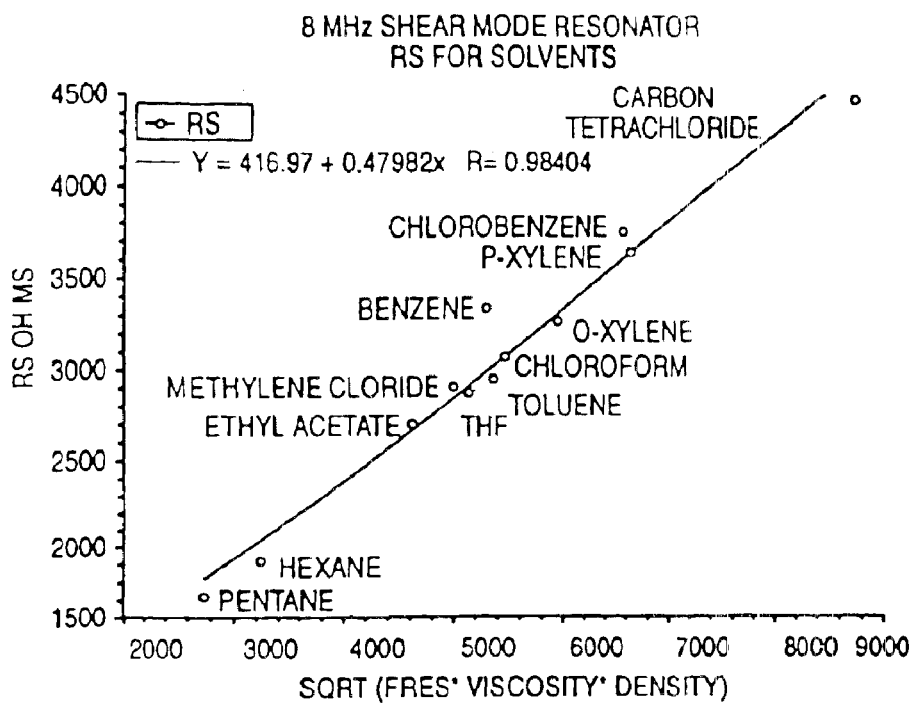
FIGS. 6a and 6b are examples of graphs illustrating the relationship between the viscosity density product and the equivalent serial resistance of the TSM resonator and the tuning fork resonator of the present invention, respectively.
Figure 6B:
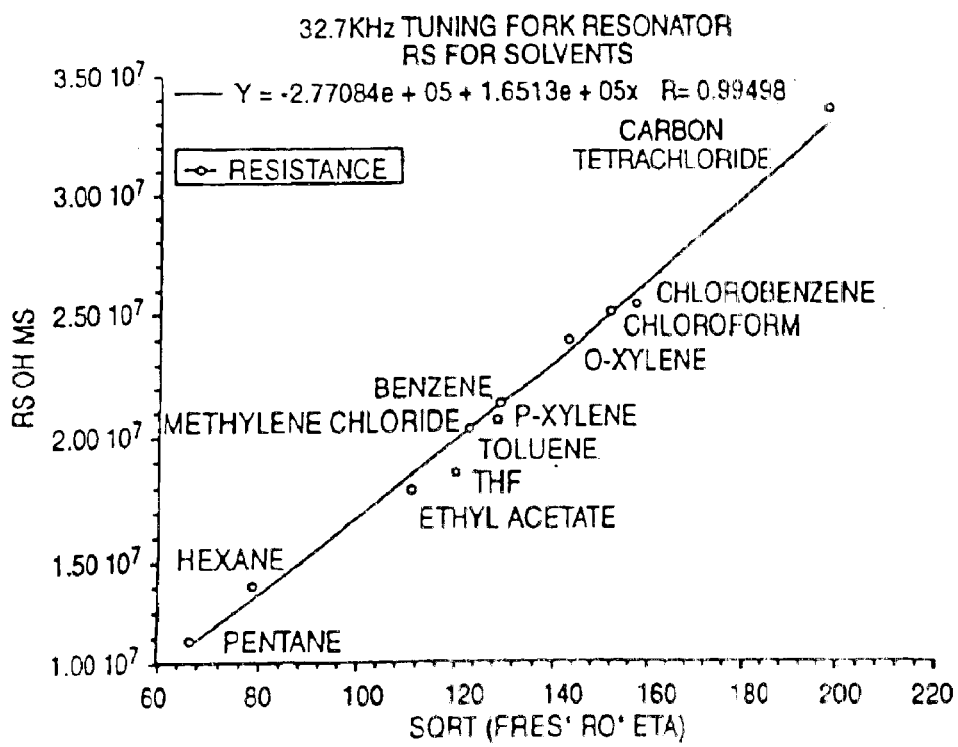

Using a tuning fork resonator 20 to measure properties of liquids also results in greater linearity in the relationship between the square root of the product of the liquid's viscosity density and the equivalent serial resistance Rs (FIGS. 6a and 6b) as well as in the relationship between the dielectric constant and the equivalent parallel capacitance Cp (FIGS. 7a and 7b) compared to TSM resonators 10. For example, the relationship between the liquid viscosity and serial resistance for a tuning fork resonator 20, as shown in FIG. 6b, is much more linear than that for the TSM resonator, as shown in FIG. 6a.

Figure 7A:
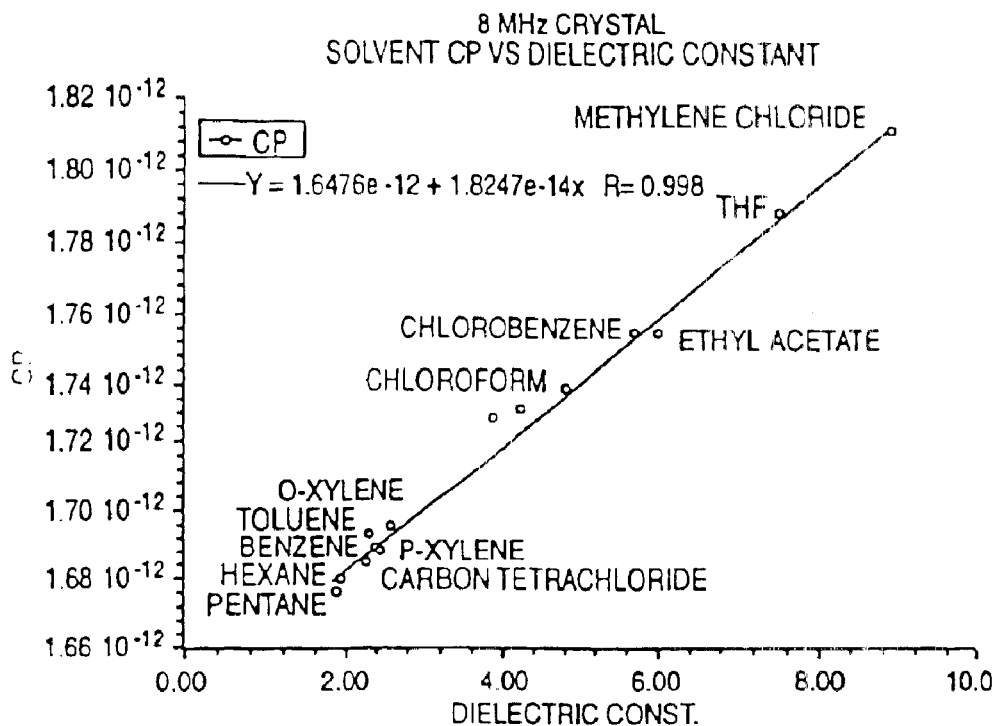
FIGS. 7a and 7b are examples of graphs illustrating the relationship between the dielectric constant and the equivalent parallel capacitance of the TSM resonator and the tuning fork resonator of the present invention, respectively.
Figure 7B:
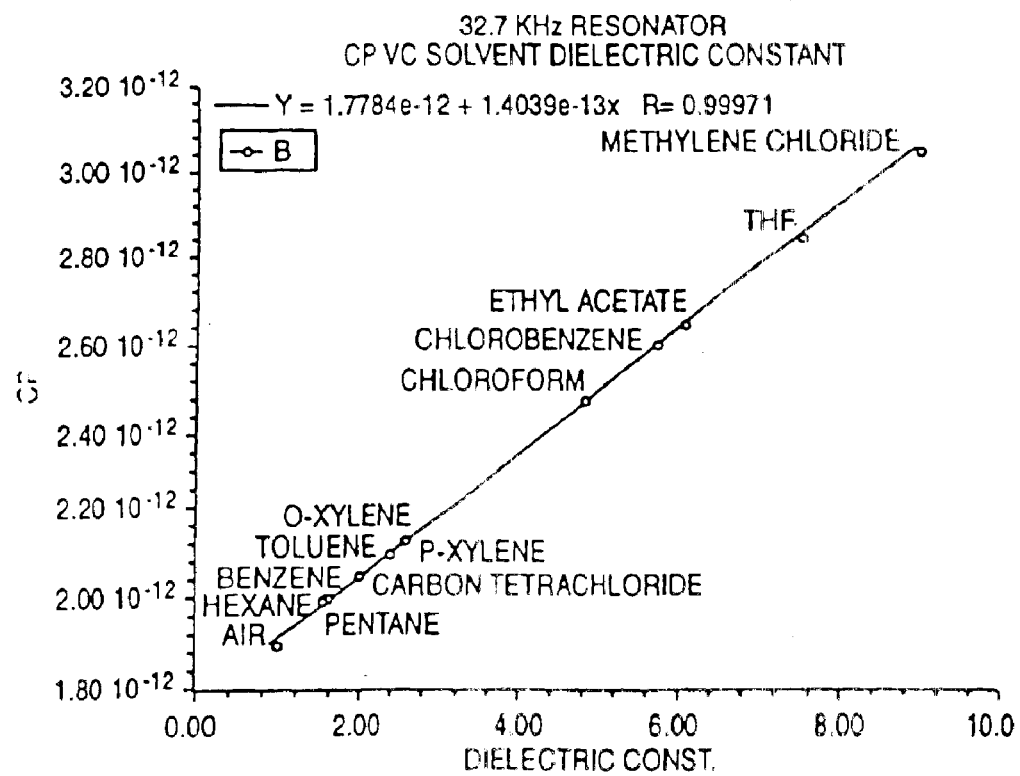

Similarly, the relationship between the dielectric constant and the equivalent parallel capacitance is more linear for a tuning fork resonator 20, as shown in FIGS. 7a and 7b. This improved linear relationship is primarily due to the relatively low frequencies at which the tuning fork resonator 20 operates; because many liquids exhibit different behavior at the operating frequencies required by the TSM resonator 10, the TSM resonator 10 will tend not to generate testing results that agree with known data about the liquids' characteristics.

Figures 8A, 8B:
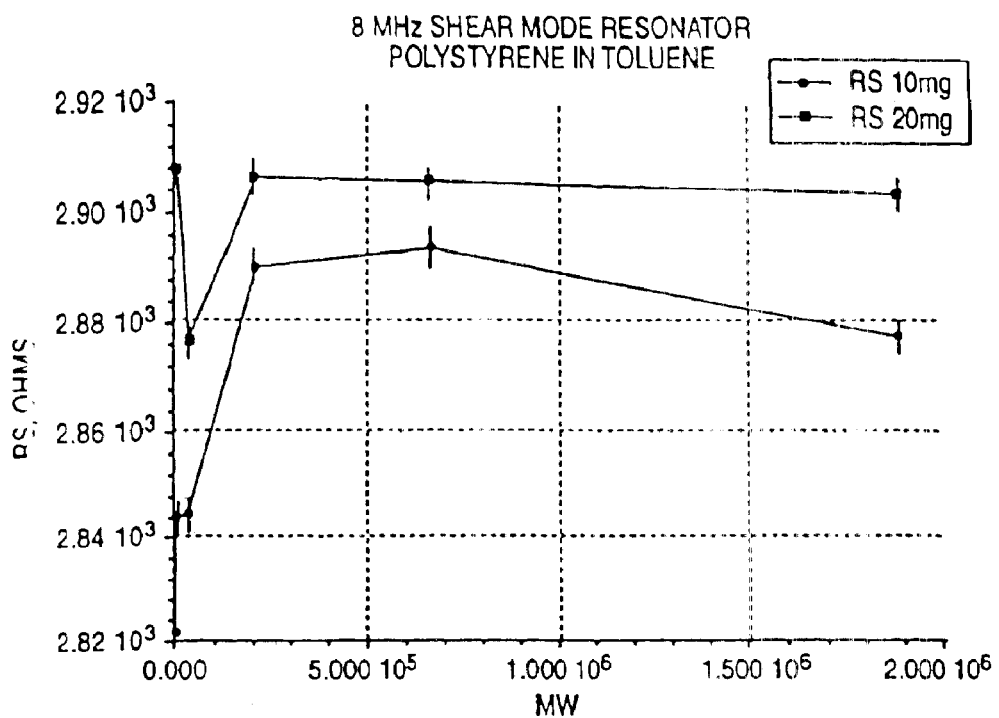
FIGS. 8a and 8b are examples of graphs illustrating the relationship between the molecular weight of a sample composition and the equivalent serial resistance of the TSM resonator and the tuning fork resonator of the present invention, respectively, in a polymerization reaction.

FIGS. 8a and 8b illustrate sample results from real-time monitoring of polymerization reactions by a TSM resonator and a tuning fork resonator, respectively. The graphs plot the equivalent resistance Rs of the resonators oscillating in 10 and 20 mg/ml polystyrene-toluene solutions versus the average molecular weight of polystyrene. As explained above, high molecular weight solutions often exhibit different physical characteristics, such as viscosity, at higher frequencies.

The size and shape of the TSM resonator 10 make the resonator suitable, but not as accurate, for real-time monitoring of polymerization reactions compared with the tuning fork resonator 20. This is because the TSM resonator's high operating frequency reduces the accuracy of measurements taken when the molecular weight of the polymerizing solution increases. As shown in FIG. 8a, a high operating frequency TSM resonator is not very sensitive in monitoring the molecular weight of the polystyrene solution used in the illustrated example. A tuning fork resonator, by contrast, has greater sensitivity to the molecular weight of the solution being measured, as shown in FIG. 8b. This sensitivity and accuracy makes it possible, for many reactions, to estimate the amount of converted solution in the polymerization reaction and use the conversion data to estimate the average molecular weight of the polymer being produced.

Figure 9A:
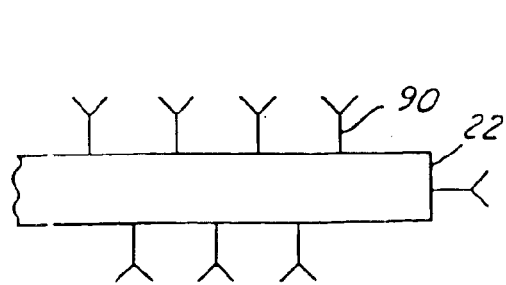
FIGS. 9a and 9b illustrate another embodiment of the invention using a resonator that is treated with a coating for targeting detection of specific chemicals.
Figure 9B:
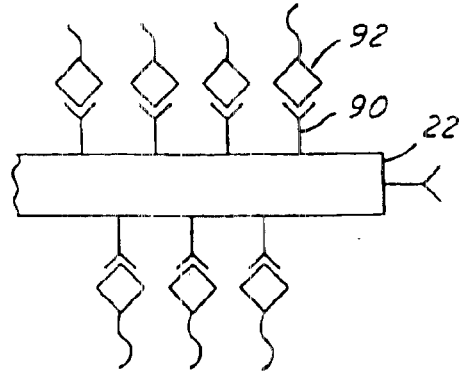

Although the above-described examples describe using a TSM or a tuning fork resonator without any modifications, the resonator can also be treated with a "functionality" (a specialized coating) so that it is more sensitive to certain chemicals. The resonator may also be treated with a general coating to protect the resonator from corrosion or other problems that could impede its performance. A representative diagram of an embodiment having a functionalized resonator is shown in FIGS. 9a and 9b. Although FIGS. 9a and 9b as well as the following description focuses on coating or functionalizing a tuning fork resonator, any other mechanical resonator can also be used without departing from the scope of the invention.

The tuning fork resonator 20 can be coated with a selected material to change how the resonator 20 is affected by a fluid composition (which, as explained earlier, includes both liquid and vapor compositions). As mentioned above, one option is a general coating for providing the tuning fork resonator 20 with additional properties such as corrosion resistance, chemical resistance, electrical resistance, and the like. Another option, as noted above, is using a "functionality", which coats the tines with materials that are designed for a specific application, such as proteins to allow the tuning fork resonator 20 to be used as a pH meter or receptors that attract specific substances in the fluid composition to detect the presence of those substances. The coating or functionality can be applied onto the tuning fork resonator 20 using any known method, such as spraying or dipping. Further, the specific material selected for the coating or functionality will depend on the specific application in which the tuning fork resonator 20 is to be used. J. Hlavay and G. G. Guilbault described various coating and functionalization methods and materials to adapt piezoelectric crystal detectors for specific applications in "Applications of the Piezoelectric Crystal Detector in Analytical Chemistry," Analytical Chemistry, Vol. 49, No. 13, November 1977, p. 1890, incorporated herein by reference. For example, applying different inorganic functionalities to the tuning fork resonator 20 allows the resonator to detect organophosphorous compounds and pesticides.

An example of a tuning fork resonator that has undergone a functionalization treatment is illustrated in FIGS. 9a and 9b. FIG. 9a represents a tuning fork tine 22 that has been treated by absorbing, coating, or otherwise surrounding the tine 22 with a functionality designed to change the tuning fork's resonance frequency after being exposed to a selected target chemical. In the illustrated example, the tuning fork tine 22 is covered with receptor molecules 90, represented in FIGS. 9a and 9b by Y-shaped members, designed to bond with specific target molecules. Because the resonance frequency and the damping of the tuning fork resonator depends on the effective mass of the tine 22 and the amount of "drag" of the tine 22 within the fluid, any change in the tine's mass or the amount of drag will change the tuning fork's resonance response. More specifically, the resonance frequency of the tuning fork resonator is proportional to the square root of the inverse of the tuning fork's mass. An increase in the tuning fork's mass will therefore reduce the tuning fork's resonance frequency.

This mass-frequency relationship is used to detect the presence of a specific target chemical in a fluid composition in this example. When the functionalized tuning fork tine 22 is placed in a fluid composition containing the target chemical, the receptors 90 on the tuning fork tine 22 will chemically bond with molecules of the target chemical 92, as shown in FIG. 9b. The resonance frequency of the tuning fork resonator will consequently decrease because of the increased mass and the additional drag created by the additional molecules 92 attached to the tuning fork tines 22 via the receptor molecules 90. Thus, when screening a plurality of fluid compositions to detect the presence of a target chemical in any of them, only the fluid compositions containing the target chemical will cause the tuning fork's resonance frequency to change. Fluid compositions without the target chemical will not contain molecules that will bond with the receptor molecules 90 on the tuning fork tine 22, resulting in no resonance frequency change for those fluids. Alternatively, the tuning fork tines 22 can be functionalized with a material that physically changes when exposed to molecules of a selected chemical such that the material changes the mechanical drag on the tuning fork tine 22 when it is exposed to the selected chemical. For example, adding a hydrophobic or hydrophilic functionality to the tuning fork tine 22 allows the tine 22 to attract or repel selected substances in the medium being analyzed, changing the mass or effective mass of the tuning fork and thereby changing its resonance frequency.

Figure 10A:
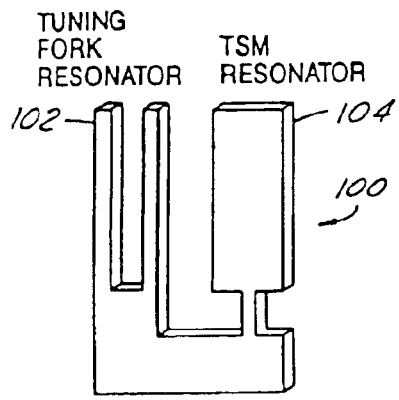
FIGS. 10a, 10b and 10c illustrate examples of different multiple resonator sensors of yet another embodiment of the present invention.
Figure 10C:
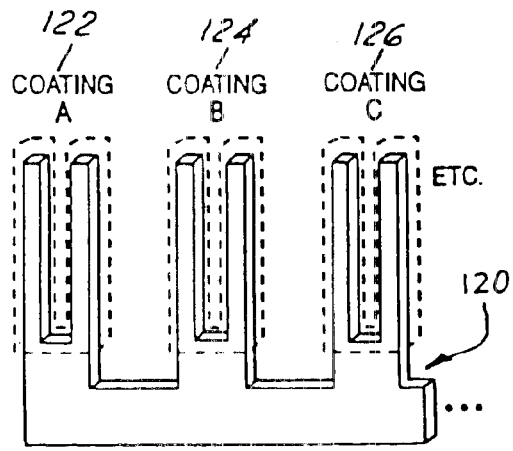
Figure 10B:
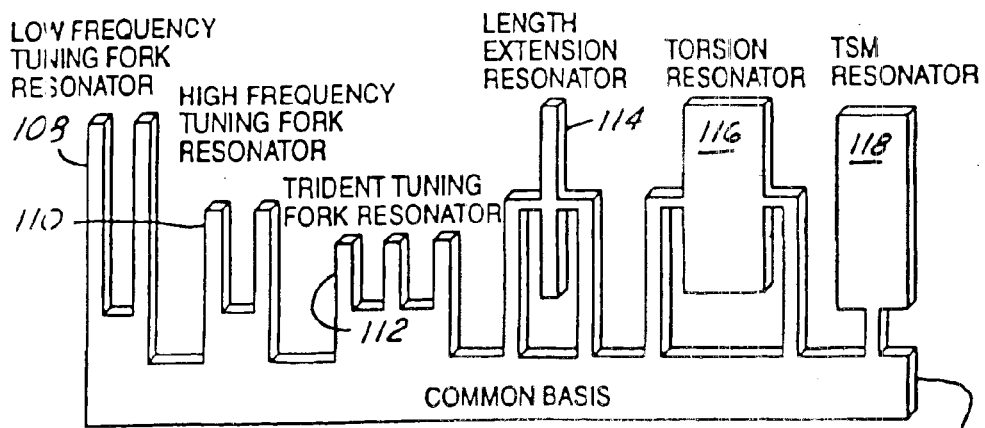

In yet another embodiment of the present invention, multiple mechanical resonators can be attached together in a single sensor to measure a wider range of responses for a given fluid composition, as shown in FIGS. 10a, 10b and 10c. The multiple resonator sensor can be fabricated from a single quartz piece such that all of the resonators are attached together by a common base, as shown in the figures. The multi-resonator sensor could also be attached to multiple frequency generating circuits, such as multiple network analyzers 28, to measure properties of the fluid compositions over multiple frequency sweeps so that the generated data can be correlated to obtain additional information about the liquid compositions. Because different resonator structures are best suited for measurement over different frequency ranges and for materials having different characteristics, a sensor combining a plurality of different resonators can provide a more complete representation of the fluid composition's characteristics over a wider frequency range than a single resonator. FIGS. 10a, 10b and 10c show specific examples of possible multi-resonator configurations, but those of skill in the art would understand that sensors having any combination of resonators can be constructed without departing from the scope of the invention.

FIG. 10a illustrates one possible sensor 100 configuration containing both a tuning fork resonator 102 and a TSM resonator 104. This type of sensor 100 can be used to, for example, measure the mechanical and electrical properties of very thick liquids such as polymer resins and epoxies. This sensor 100 can also be used to monitor a material as it polymerizes and hardens. For example, the sensor 100 can be placed in a liquid composition containing urethane rubber in its diluted state so that the tuning fork 102 is used initially to measure both the composition's density viscosity product and its dielectric constant. As the rubber changes to a gel and finally to a solid, the sensor 100 can switch to using the TSM resonator 104 to measure the rubber's mechanical properties, leaving the tuning fork resonator 102 to operate as a dielectric sensor only.

A sensor 106 for observing a fluid composition over a wide frequency range is shown in FIG. 10b. High polydispersity polymer solutions are ideally measured over a wide frequency spectrum, but most resonators have optimum performance within a relatively limited frequency range. By combining different resonators having different resonance frequencies and different response characteristics, it is possible to obtain a more complete spectrum of resonator responses for analyzing the fluid's characteristics under many different conditions. For example, due to the wide spectrum of polydisperse solution relaxation times, it is generally predicted that high molecular weight compositions will react at lower frequencies than lighter molecular weight compositions. By changing the temperature, observing the frequency response of different resonators, and correlating the different resonator responses, it is possible to obtain a more accurate picture of a composition's relaxation spectrum than from a single resonator.

A low frequency tuning fork resonator 108 and a high frequency tuning fork resonator 110 in one sensor will probably suffice for most wide-frequency range measurements. For certain cases, however, the resonators in the multi-resonator sensor 106 can also include a trident tuning fork resonator 112, a length extension resonator 114, a torsion resonator 116, and a TSM resonator 118, membrane oscillators, bimorphs, unimorphs, and various surface acoustic wave devices, as well as any combination thereof, or even a single resonator structure than can operate in multiple mechanical modes (e.g. compression mode, axial mode, torsion mode). Of course, not all of these resonators are needed for every application, but those of skill in the art can select different combinations that are applicable to the specific application in which the sensor 106 will be used.

Alternatively, multiple resonators having the same structure but different coatings and/or functionalities can be incorporated into one sensor 120, as shown in FIG. 10c. In this example, a plurality of tuning fork resonators 122, 124, 126 have the same structure but have different functionalities, each functionality designed to, for example, bond with a different target molecule. The high sensitivity of the tuning fork resonators 122, 124, 126 makes them particularly suitable for "artificial noses" that can detect the presence of an environmentally-offending molecule, such as hydrogen sulfide or nitrous oxide, in industrial emissions. When the sensor 120 is used in such an application, one tuning fork resonator 122 can, for example, be functionalized with a material designed to bond with hydrogen sulfide while another resonator 124 can be functionalized with a material designed to bond with nitrous oxide. The presence of either one of these molecules in the fluid composition being tested will cause the corresponding tuning fork resonator 122, 124 to change its resonance frequency, as explained with respect to FIGS. 9a and 9b.

The tuning fork resonators 122, 124, 126 can also be functionalized with a polymer layer or other selective absorbing layer to detect the presence of specific molecules in a vapor. Because the tuning fork resonators 122, 124, 126 are highly sensitive to the dielectric constant of the surrounding fluid, the tuning fork resonators 122, 124, 126 can easily detect changes in the dielectric constant of the fluid and recognize a set of solvents with different dielectric constants in the fluid. This information, combined with other observable parameters, makes tuning fork resonators particularly adaptable for use in artificial noses.

The method and system of the present invention has been described above in the combinatorial chemistry context, but it is not limited to such an application. Because the resonators in the method and system of the present invention have high sensitivities and quick response times, it can be also be used for in-line monitoring of fluid compositions flowing through conduits or pipelines. For example, the invention can be used in a feedback system to monitor properties of liquids flowing through a gas or oil pipeline to monitor and control the concentration of additives in the gas or oil, or to detect the presence of impurities in water flowing through a water pipe. The additives or impurities will change the physical and electrical characteristics of the liquid flowing through the conduit. A functionalized tuning fork resonator 20 can further detect the presence of a specific chemical in a fluid composition, whether it is a liquid or a vapor, and can be used to monitor the presence of, for example, a known chemical pollutant in a smokestack. The high sensitivity and quick response time of the resonator, and the tuning fork resonator 20 in particular, makes it uniquely suitable for such an application. The circuitry and system used to generate the visual traces from the resonator's response can be the same as described above or be any other equivalent resonator analysis system.

Further, although the above description focuses primarily on using TSM resonators and tuning fork resonators, any other mechanical resonators exhibiting similar characteristics can be used. Tridents, cantilevers, torsion bars, bimorphs, and/or membrane resonators can be substituted for the TSM resonator or tuning fork resonator without departing from the scope of the claimed invention.

It should be understood that various alternatives to the embodiments of the invention described herein may be employed in practicing the invention. It is intended that the following claims define the scope of the invention and that the methods and apparatus within the scope of these claims and their equivalents be covered thereby.

We claim:

1. A method for in-line monitoring of a fluid composition, the method comprising:

placing a tuning fork resonator in contact with the fluid composition in a conduit;

oscillating the resonator while the fluid composition is flowing in the conduit;

monitoring the resonator to obtain a resonator response; and determining at least two properties of the fluid composition based on the resonator response, where at least one of the properties is an electrical property.

2. The method of claim 1, wherein at least one of the two properties is selected from the group consisting of viscosity, viscosity density product, molecular weight, or specific weight.

3. The method of claim 2, wherein the at least two properties are separately determined based on the resonator response.

4. The method of claim 3, wherein the separately determining step included separately determining at least three properties of the fluid composition.

5. The method of claim 4, wherein the at least three properties are viscosity, dielectric constant and conductivity.

6. The method of claim 2, wherein one of the at least two properties is viscosity.

7. The method of claim 2, wherein the at least two properties are viscosity and dielectric constant.

8. The method of claim 2, further comprising:
calibrating the resonator against a standard fluid or a number of standard fluids having known properties to obtain calibration data; and
determining the at least two properties based on the calibration data and the resonator response.

9. The method of claim 8, wherein the conduit is an oil pipeline.

10. The method of claim 1, wherein the fluid composition comprises a liquid.

11. A method for in-line monitoring of a fluid composition, the method comprising:
calibrating a tuning fork resonator against a standard fluid or a number of standard fluids having known properties to obtain calibration data;
placing the resonator in contact with the fluid composition in a conduit;
oscillating the resonator while the fluid composition is flowing the conduit;
monitoring the resonator to obtain a resonator response; and
determining at least two properties based on the calibration data and the resonator response, where at least one of the properties is an electrical property.

12. The method of claim 11, wherein one of the at least two properties is viscosity.

13. The method of claim 11, wherein the at least two properties are viscosity and dielectric constant.

14. The method of claim 11, wherein the fluid composition comprises a liquid.

* * * * *

UNITED STATES PATENT AND TRADEMARK OFFICE
CERTIFICATE OF CORRECTION

PATENT NO. : 6,957,565 B2
DATED : October 25, 2005
INVENTOR(S) : Matsiev et al.

It is certified that error appears in the above-identified patent and that said Letters Patent is hereby corrected as shown below:

<u>Title page,</u>
Item [56], References Cited, OTHER PUBLICATIONS, replace
"Hiavay, J. and G.G. Guilbault, "Applications of the Piezo-"" with
-- Hlavay, J. and G.G. Guilbault, "Applications of the Piezo-" --.

Signed and Sealed this

Tenth Day of January, 2006

JON W. DUDAS
*Director of the United States Patent and Trademark Office*